United States Patent
Lin

(10) Patent No.: US 8,658,629 B2
(45) Date of Patent: Feb. 25, 2014

(54) **USE OF LANOSTANE AND *PORIA* EXTRACT IN TREATING CACHEXIA**

(75) Inventor: Hang-Ching Lin, Taipei (TW)

(73) Assignee: Sinphar Tian-Li Pharmaceutical Co., Ltd., Zhejiang (CN)

( * ) Notice: Subject to any disclaimer, the term of this patent is extended or adjusted under 35 U.S.C. 154(b) by 696 days.

(21) Appl. No.: 12/771,777

(22) Filed: Apr. 30, 2010

(65) Prior Publication Data

US 2010/0279992 A1 Nov. 4, 2010

(30) Foreign Application Priority Data

May 2, 2009 (CN) .......................... 2009 1 0140562

(51) Int. Cl.
*A61K 31/56* (2006.01)
(52) U.S. Cl.
USPC .......................................... 514/180; 514/182
(58) Field of Classification Search
USPC ................................................ 514/180, 182
See application file for complete search history.

(56) References Cited

U.S. PATENT DOCUMENTS

2004/0086580 A1* 5/2004 Tripp et al. ................... 424/745
2004/0229852 A1 11/2004 Lin et al.

OTHER PUBLICATIONS

Zhou et al., Chem. Pharm. Bull., Oct. 2008;56(10):1459-1462.*
English abstract of Jankowska et al., Wiad Lek., 2003;56(7-8):308-312.*

Kamei, et al., "*The Effect of a Traditional Chinese Prescription for a Case of Lung Carcinoma*", Journal of Alternative and Complementary Medicine (New York, NY) Dec. 2000, LNKD-PUBMED: 22252062, vol. 6, No. 6, Dec. 2000, pp. 557-559.
Zee-Cheng, "*Shi-Quan-Da-Bu-Tan (Ten Signifcant Tonic Decoction), SQT. A Potent Chinese Biological Response Modifier in Cancer Immunotherapy, Potentiation and Detoxification of Anticancer Drugs*", methods and Findings in Experimental and Clinical Pharmacology, Prous, Barcelona, ES, vol. 14, No. 9, Nov. 1, 1992, pp. 725-736.
Aburada, et al., "*Protective Effects of Juzentaihoto, Dried Decoctum of 10 Chinese Herbs Mixtures, Upon the Adverse Effects of Mitomycin C in Mice*", Journal of Phamacobio-Dynamics, Tokyo, JP, vol. 6, No. 12, Dec. 1, 1983, pp. 1000-1004.
Zhang Min et al., "*Pharmacological Mechanisms and Advancement of Poria cocos.*" Journal of Beihua University (Natural Science Edition) (Chinese) Feb. 2008, vol. 9, No. 1, pp. 63-68.
Lin Dongxing, "*Research of Ganoderma Lucidum in Adjunctive Therapy of Cancer.*" Edible Fungi of China (ChINESE). 2000, vol. 19, No. 1, pp. 3-5.
Zeng et al., "*Advances of Researches on Triterpene Constituents and Pharmacology of Ganoderma Lucidum.*" Journal of Fungal Research (Chinese). 2004, vol. 2, No. 1, pp. 68-77.
Bai et al., Review on the Research of Cancer Cachexia. Zhejiang JITCWM (Chinese). 2003, vol. 13, No. 3, pp. 197-199.

* cited by examiner

*Primary Examiner* — San-Ming Hui
(74) *Attorney, Agent, or Firm* — Cesari and McKenna, LLP

(57) ABSTRACT

A pharmaceutical composition for treating cachexia, and in particular for treating cancer cachexia. The composition contains a lanostane compound as a potent component. A suitable source of the lanostane compound is a *Poria* extract from metabolite, sclerotium, or fermentation product of *Poria cocos* (Schw) Wolf. The *Poria* extract contains 1-60% of the lanostane compounds by weight of the extract, and is devoid of secolanostane.

20 Claims, 4 Drawing Sheets

USE OF LANOSTANE AND *PORIA* EXTRACT IN TREATING CACHEXIA

CROSS-REFERENCE TO RELATED APPLICATION PARAGRAPH

This application claims the benefit of Chinese Patent Application No. 200910140562.5, filed on May 2, 2009, the content of which is hereby incorporated by reference in its entirety.

FIELD OF THE INVENTION

This invention related to a pharmaceutical composition for prophylaxis and/or treating of wasting diseases (such as cachexia and anorexia), and in particular to a cachexia caused by a cancer. The pharmaceutical composition of this invention comprises a lanostane compound as active ingredient. A proper source of the lanostane compound is a *Poria* extract. Further, the lanostane compound may obtain from *Cordyceps sinensis, Antrodia cinnamomea* or *Granodema lucidum*.

BACKGROUND OF THE INVENTION

Cachexia is a state with an unhealthy fatigue state, and is usually caused by anorexia from diseases and changes of endocrine system and immune system, resulting in wasting, loss of muscle and visceral proteins, finally in loss of body weight.

Cachexia is a syndrome used to be found in patients with chronic diseases or critical care. In particular to patients with stomach cancers or pancreas cancers among patients with cancers, and there are about 70% patients who will develop this syndrome. At the late stage of cancer, there are about 80% patients who will develop cachexia no matter what kind cancer they have. Cachexia is characterized by that there is no way to prevent or terminate loss of patients' body weight, even if you increase the food amount and enhance the nutrients intake for the patient. Hormonal appetite enhancer (such as megestrol, medroxyprogesterone acetate) is usually used in the treatment, however, someone has pointed out that it only results to a temporary increase of body weight (water and fat increase only), and there is no increase of body muscle, and there is no improvement on activity ability and physical activity. Contrarily, some drug side-effects are observed such as thrombus, edema, hemorrhage, hyperglycemia and hypertension and the like.

Catabolic wasting or cachexia is a syndrome characterized by spontaneously progressive wasting of fat and skeletal muscle, refractory body weight loss to increase nutrition import, increase of resting energy expenditure (REE), decrease of protein synthesis, change of carbohydrate metabolism (Cori cycle activity increase), over catabolism of ATP-ubiquitin dependent proteasomes pathway through protein solvent, and over catabolism of adipose tissue through adipose solvent (Body J J, Curr Opin Oncol 11: 255-60, 1999, Muscaritoli M, et al: Eur J Cancer 42: 31-41, 2006). In general, a patient will not be diagnosed cachexia until 5% or 5 pounds body weight loss at least. About half of patients with cancers experience certain level of catabolic wasting, and a higher attack rate is found in the cases with lung, pancreas and gastrointestinal malignant diseases (Dewys W D, et al: Am J Med 69: 491-7, 1980). The syndrome is found in patients with immunodeficiency diseases such as AIDS and patients with bacterial and parasitic diseases, rheumatoid arthritis, chronic diseases associated with bowel, liver, lung and heart. Cachexia also relates to anorexia, which may be a situation of aging or a result of body injury or burn. Cachexia syndromes reduce patients' functional ability and living quality, deteriorate potent situation, and reduce drug tolerance. The level of cachexia is inverse proportional to the survival time of patient, which usually means a poor prognosis. In recent years, diseases associated aging and disable has become a major issue in health care.

Anorexia (a medical term for appetite loss) is a deterioration of many malignant diseases, and is often found in patients with cancer, infectious diseases, chronic organ failure and trauma. Anorexia is a sever syndrome because it will cause a decrease calorie intake and dystrophy. Symptoms of anorexia include decrease of gestation and olfaction, early satiety, decrease of hunger sensation and even complete food aversion, and nausea and vomit may be found in some cases. The reasons of anorexia are not well known, and there are only limited options available for effective therapy. Some research has mentioned that a combination of hormone, social factor and psychological factor might be an important factor for the onset and progression of this syndrome.

It is not clarified a consistent relationship between cachexia onset and tumor size, disease stage, type and period of a malignant disease although cachexia is usually associated with cancer actually. The cancer cachexia usually associates with decrease of calorie intake, increase of resting energy expenditure, and metabolic change of protein, fat and carbohydrate. For example, some significant abnormality of carbohydrates includes: increase of total glucose conversion, increase of glyconeogenesis, glucose impaired tolerance and hyperglycemia. It is usually found an increase of fat solvent, increase conversion of free fatty acid and glycerol, hyperlipidemia, and decrease of lipoprotein lipase activity. It should be concerned that cachexia-associated body weight loss is not only caused by body fat storage loss but also related to body total protein mass loss and pervasive skeletal muscle wasting. An increase of protein conversion and impaired regulation of amino acid oxidation might be critical factors for this syndrome deterioration. Further, specific host influence factors produced corresponding to cancers, such as pro-inflammatory cytokines (tumor necrosis factor-α (TNF-α), interleukin-1, interleukin-6 and γ-interferon), acute phase protein (e.g. C-reactive protein) and specific prostaglandin, are likely to associate with cancer cachexia.

In Chinese traditional herbal medicine, it is recommended that aged people take *Poria galenical* everyday, and it will help aged people to delay aging and have long life in addition to not easy to be sick.

The applicant of the present application in EP 1535619 A1 discloses a pharmaceutical composition for enhancing immunity in human body, which contains a lanostane compound as a potent component. This composition is able to enhance immunity and is useful in the prophylaxis and treatment of virus infections. On the other hand, the *Poria* extract and lanostanes purified therefrom show an inhibition effect on immunity, and are used in the prophylaxis and treatment of IgE-mediated allergies (asthma). This inhibition effect is disclosed in US2009 0318399 A1 and WO 2009/155/730 A1. These applications indicate that *Poria* extract and lanostanes are able to adjust immunity. The applicant of the present application in US 2009/0247496-A1 and WO 2009/124420 A1 discloses that *Poria* extract and lanostanes purified therefrom have an effect on human intestines and enhance the uptake of nutrients: absorption of glucose, amino acids, and vitamins (folic acid).

Therefore, *Poria* extract ingredient, particularly lanostane compounds, might help in improving and treating cachexia associated with nutrition and immunology. In this invention, whether or not the *Poria* extract ingredient and lanostane compounds have a treating effect on cachexia was evaluated by performing experiments with mice transplanted with human lung cancer cells, wherein the human lung cancer cell transplanted mice were observed as to whether they had normal appetite and had normal body weight without gradually losing their body weight in comparison with normal mice.

SUMMARY OF THE INVENTION

A primary objective of the present invention is to provide a pharmaceutical composition of prophylaxis or treatment of a wasting disease (such as cachexia and anorexia), and in particular to a cachexia caused by a cancer.

Another objective of the present invention is to provide a use of *Poria* extract prepared from *Poria cocos* (Schw) Wolf in the prophylaxis or treatment of a wasting disease (such as cachexia and anorexia), and in particular to a cachexia caused by a cancer.

A further objective of the present invention is to provide a new use of lanostane in the prophylaxis or treatment of a wasting disease (such as cachexia and anorexia), and in particular to a cachexia caused by a cancer.

A method for the prophylaxis or treatment of a wasting disease (such as cachexia and anorexia) disclosed in the present invention comprises administering to a mammal in need thereof an effective amount of a lanostane compound having the following chemical formula (I), or a pharmaceutically acceptable salt thereof:

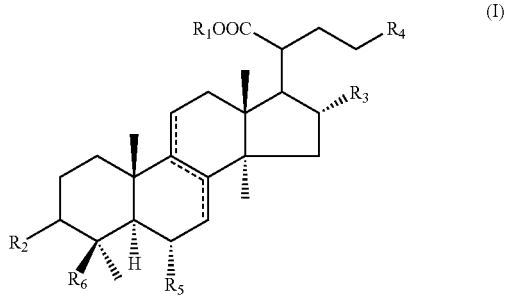

(I)

wherein $R_1$ is —H or —$CH_3$; $R_2$ is —$OCOCH_3$, =O, or —OH; $R_3$ is —H or —OH; $R_4$ is —C(=$CH_2$)—C($CH_3$)$_2R_a$, wherein $R_a$ is —H or —OH, or —CH=C($CH_3$)$R_b$, wherein $R_b$ is —$CH_3$ or —$CH_2OH$; $R_5$ is —H or —OH, and $R_6$ is —$CH_3$ or —$CH_2OH$.

Preferably, the lanostane compound (I) has the following chemical formula:

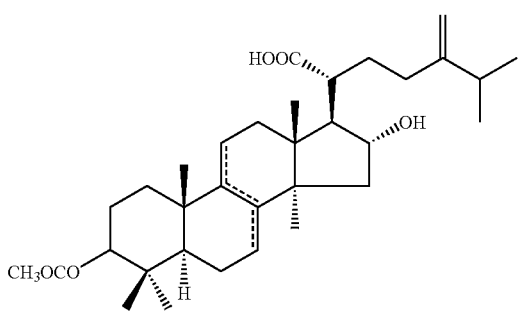

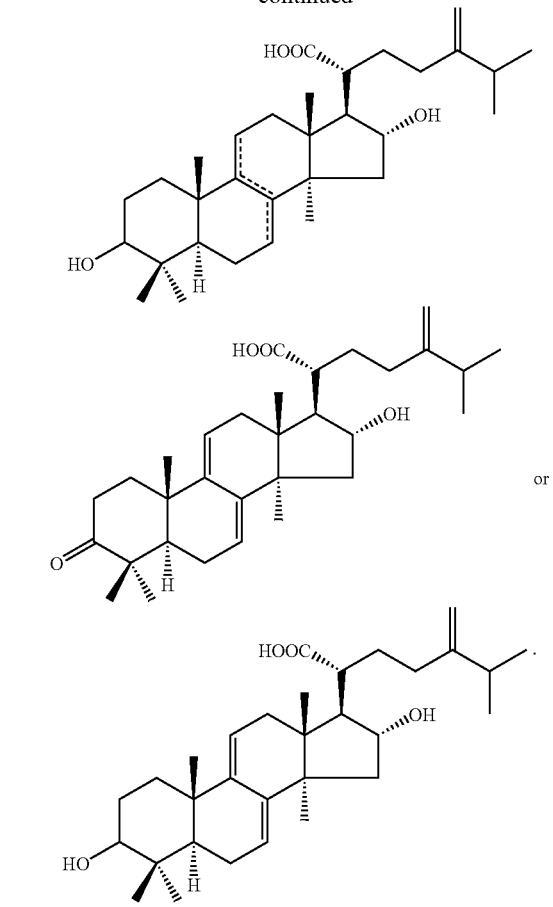

Preferably, the lanostane compound (I) is administered to the mammal as a *Poria* extract comprising 1-60% of the lanostane compound (I), based on the weight of the *Poria* extract. More preferably, said *Poria* extract is substantially free of secolanostane. Most preferably, said *Poria* extract comprises, based on the weight of the *Poria* extract, 5-35% of the lanostane compound (I).

Preferably, said *Poria* extract is prepared by a method comprising the following steps:

a) extracting metabolites, fermentation products or sclerotium of *Poria cocos* (Schw) Wolf by water, methanol, ethanol, or a mixed solvent thereof;

b) concentrating the resulting liquid extract from step a);

c) introducing the resulting concentrated substance from step b) into a silica gel column;

d) eluting the silica gel column with an eluent having a low polarity, and collecting the resulting eluate; and e) concentrating the eluate to form a concentrated eluate.

Preferably, the concentrated eluate from step e) has a chromatographic value, Rf, not less than 0.1 in accordance with a thin layer chromatography, which is developed by a mixed solvent of dichloromethane:methanol=96:4 and is detected by an ultraviolet lamp and iodine vapor.

Preferably, the extraction in step a) is carried out by using 95% ethanol.

Preferably, the extraction in step a) comprises extracting metabolites, fermentation products or sclerotium of *Poria cocos* (Schw) Wolf by boiling water; adding a base to the resulting extraction aqueous solution until a pH value thereof is 9-11; recovering the basic aqueous solution; adding an acid to the basic aqueous solution until a pH value thereof is 4-6 to form a precipitate; recovering the precipitate; extracting the precipitate with ethanol; and recovering a liquid extract.

Preferably, the concentrated substance resulted from step b) is further extracted with a two-phase solvent containing methanol and n-hexane in a volumetric ratio of 1:1, a methanol layer is separated from the two-phase solvent extraction mixture, and the methanol layer is concentrated to form a concentrate, which is used as a feed to the silica gel column in step c).

Preferably, the low polarity eluent in step d) is a mixed solvent containing dichloromethane and methanol in a volumetric ratio of 96.5:3.5.

Preferably, the lanostane compound (I) is administered together with a nutrient, for examples glucose, an amino acid, a vitamin, or a combination thereof.

Preferably, the lanostane compound (I) or a pharmaceutically acceptable salt thereof is administered to the mammal as an isolated compound together with a pharmaceutical acceptable carrier or diluent.

Preferably, the administering is oral intake.

Preferably, the mammal is a human.

Preferably, the wasting disease of the present invention is a cachexia; more preferably, the cachexia is caused by a cancer, such as lung cancer, stomach cancer, pancreas cancer, colorectal cancer, breast cancer, oral cavity cancer or nasopharyngeal cancer.

Preferably, the wasting disease of the present invention is caused by cancer, anorexia, aging, body injury or burn.

Preferably, the administration of lanostane (I) or a pharmaceutically acceptable salt thereof is not less than 8.4 mg/day.

The present invention use a lanostane compound represented by formula (I) or pharmaceutically acceptable salt thereof, or the above *Poria* extract to treat anorexia, serious loss of boty weight in cancer patients. In addition to cancer, cachexia-associated diseases include the cachexia caused by AIDS, aging, rheumatoid arthritis, pulmonary tuberculosis, fibrocyst, Crohn's disease, infective diseases and the like. It is required to have a nutrient supplement (amino acids, glucose, and vitamins) to improve the wasting state caused by surgery or cancer patients who receive chemotherapy or radiotherapy. The active ingredient of the present invention may be added into milk powder, drink, or food for the purpose of nutritional supplement. Also, it may be formulated into a tablet, capsule, granules, liquor, injection and the like, for medicinal purpose.

DETAILED DESCRIPTION OF THE INVENTION

Figure 1:
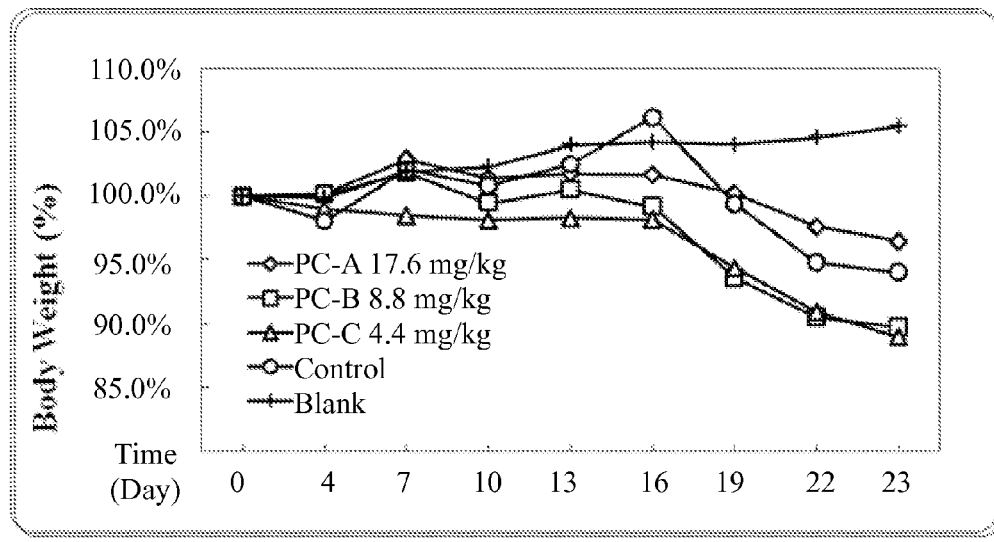
FIG. 1 shows body weight changes of mice in each group mice in the first test in Example 7, wherein + represents the blank group; black circle represents the control group; and diamond, square and triangle respectively represent the drug administration groups PC-A, PC-B and PC-C, wherein mice were administered lanostane in an amount of 17.6 mg, 8.8 mg and 4.4 mg per kg body weight, respectively.

Cachexia means human body is at a fatigue state, and the reasons causing cachxia have many theories; however there is no such a mechanism can be assured. As to cancer, it is known so far that cancer cells release factors or the immune reaction of human body to cancer cells will cause release of various factors, either directly or indirectly, resulting in anorexia, creating changes of endocrine system and immune system in the human body, so that patients start dislike food intake, and thus fat and proteins in muscles gradually decrease, which lead to phenomena of body fragile gradually and body weight loss gradually.

Cachexia-associated diseases include cancer, infectious disease (such as pulmonary tuberculosis, AIDS), autoimmune diseases (rheumatoid arthritis), aging, fibrocyst, and Crohn's disease. There are about 70% of the cancer patients who will develop this syndrome, and more often found in patients with stomach cancer and pancreas cancer. At the late stage of cancer, there are about 80% of the cancer patients who will develop cachexia no matter what kind cancer they have. There is no way to prevent or terminate loss of patients' body weight, even if increasing the food intake or other methods through gavages or intravenous injection to increase nutrition have been applied in the treatment. Hormone appetite enhancer (such as megestrol, medroxyprogesterone acetate) is usually used in the treatment; however, someone has risen that it only results in a temporary increase of body weight (water and fat increase only), and there is no increase of body muscle, and there is no improvement on physical activity. Contrarily, some drug side-effects are observed such as thrombus, edema, hemorrhage, hyperglycemia and hypertension.

An extract of *Poria* for enhancing nutrient uptake by mammals (for example, humans) disclosed in the present invention can be prepared by a process similar to that disclosed in US2004/0229852 A1, which includes extracting *Poria cocos* (Schw) Wolf with the conventional extraction methods to obtain a crude extract, separating the crude extract by chromatography into a low polarity fraction of lanostane (with an eluent of dichloromethane:methanol of 96:4) and a high polarity fraction of secolanostane (with eluents of dichloromethane:methanol of 90:10, and 0:100), wherein the lanostane fraction is detected by a thin layer chromatography having a chromatographic value, Rf, not less than 0.1 in accordance, when it is developed by a mixed solvent of dichloromethane:methanol=96:4; the Rf is less than 0.1 for the secolanostane fraction. Several lanostanes are separated from the lanostane fraction by subjecting the lanostane fraction to silica gel column chromatography eluted, wherein the eluents used are dichloromethane:methanol=97:3 to 95:5.

The following examples are provided for describing the present invention in further details, but should not be used to limit the scope of the present invention.

Percentages and other amounts referred to in this specification are by weight unless indicated otherwise. Percentages are selected from any ranges used to total 100%.

Example 1

26 kg of *Poria* grown in Yunnan was extracted with 260 liters of 75% aqueous alcohol solution under heating. The extraction were repeated three times; the resulting three extraction solutions were combined and vacuum concentrated to yield an extract of 225.2 g. Quantitative analyses were subsequently carried out on the extract, which indicated that 76.27 mg of lanostanes could be found in every gram thereof, wherein K1 (pachymic acid) took up 33.4 mg; K1-1 (dehydropachymic acid) took up 9.59 mg; K2-1 (tumulosic acid) occupied 19.01 mg; K2-2 (dehydrotumulosic acid) occupied 6.75 mg; K3 (polyporenic acid C) occupied 5.06 mg, and K4 (3-epidehydrotumulosic acid) occupied 2.46 mg.

Example 2

125 g of the alcohol extract from Example 1 was further extracted six times with 1.3 liters of dichloromethane; the resulting six extraction solutions were combined and concentrated to obtain an extract of 22.26 g. The dichloromethane extract were dissolved in heated 95% alcohol and left to cool, followed by filtering and discarding the insoluble substances. A small amount of water was added into the filtrate until the alcohol concentration reached 45% therein, which resulted in precipitation; from which a precipitate of 17.4 g was obtained by centrifugation consequently. Subsequent quantitative analyses on the precipitate indicated that each gram thereof comprised 264.78 mg of lanostanes, wherein K1-1 occupied 159.7 mg; K1-2 occupied 56.96 mg; K2-1 occupied 24.43 mg; K2-2 occupied 8.8 mg; K3 occupied 9.84 mg, and K4 occupied 5.05 mg. The method of thin layer chromatography (TLC) with silica gel was used to confirm the precipitate did not comprise any secolanostane.

Example 3

100 kg of *Poria* was boiled with 800 kg of water for 3 hours, then left for cooling to 50° C. and a pH value thereof was adjusted to pH 11 by using a 5N NaOH solution, followed by stirring the resulted solution for 3 hours. A centrifugation machine was used to separate the liquid from the solid, followed by adding another 800 kg of water to the separated solids. The aforesaid procedures were repeated, including adjusting pH value with NaOH to pH 11, stirring, and removing the solids by centrifugation. The two resulting liquids were combined, and then vacuum concentrated to a solution of 100 kg at 50° C., followed by the adjustment of pH value to pH 6.5 by using 3N HCl so as to produce a precipitate. Said precipitate was separated from the solution, subsequently rinsed with 40 L H2O, and centrifuged in order to recover the precipitate; the precipitate was sprayed dry with 8 L of water, which yielded 380 g of powder. Afterwards, the powder was extracted three times by using 4 L of alcohol, and the extraction solutions were combined and concentrated to result in 238.9 g of alcohol extract. The 238.9 g of alcohol extract was proved containing no secolanostane compounds by the TLC analysis, and then was subjected to HPLC separation, which gave 214 mg of K2, 23 mg of K3, 24 mg of K4, and 4.52 mg of K1 in per gram of the extract. In other words, each gram of the extract has approximately 265 mg of lanostane compounds.

Or the powder was extracted by using 4 L of 50% aqueous alcohol solution, and then had the 50% aqueous alcohol solution removed in order to obtain an insoluble powder; the extraction was repeated three times to yield 245.7 g of a substance insoluble in 50% aqueous alcohol solution. The insoluble substance was confirmed having no secolanostane compounds by the TLC analysis, and then underwent separation and purification processes by HPLC, which yielded 214 mg of K2, 23 mg of K3, 24 mg of K4, and 4.52 mg of K1 in each gram of the extract, which is equivalent to approximately 261 mg of lanostane compounds in each gram of the extract.

Example 4

A *Poria* powder was made of 30 kg of the China-grown *Poria cocos* (Schw) Wolf. The *Poria* powder was extracted with 120 L 95% alcohol for 24 hours. The mixture was filtered to obtain a filtrate. The residue was extracted and filtered for another three cycles. The filtrates were combined and concentrated to bring about a dried extract in an amount of 265.2 g. The dry extract underwent a distribution extraction with a two-phase extraction agent (n-hexane:95% methanol=1:1), and the methanol layer was removed therefrom, which is then concentrated to obtain a dry solid in an amount of 246.9 g. A separation of the dry solid was carried out by means of a silica gel column, which was filled with silica gel 10-40 times of the weight of the dry solid. The silica gel having a diameter of 70-230 mesh was made by Merck Corporation with a code of Silica Gel 60. The column was eluted by the following eluates in sequence: a mixed solvent of dichloromethane:methanol=96:4; a mixed solvent of dichloromethane:methanol=90:10, and pure methanol. The eluates were tested by the thin layer chromatography (TLC), wherein an ultraviolet lamp and iodine vapor were used for detecting, and a mixed solvent of dichloromethane:methane=96:4 was used as a developing liquid. The eluates having similar constituents in the TLC were combined.

The elution carried out with the mixed solvent of dichloromethane:methanol=96:4 resulted in a PCM portion in an amount of 78 g. The PCM showed 6 trace points in the thin layer chromatography. The resulted eluates from the elutions carried out with the eluents of dichloromethane:methanol=90:10 and pure methanol were combined to obtain a PCW portion in an amount of 168 g.

The PCM portion was further separated by means of an eluent of dichloromethane:methanol=96.5:3.5 and the same silica gel column to obtain purified lanostane components of K1 (K1-1 and K1-2), K2 (K2-1 and K2-2), K3, K4, K4a, K4b, K5, K6a and K6b. Further details of the separation steps and identification analysis data can be found in US2004/0229852 A1.

The aforesaid K1 to K6b compounds have the following structures:

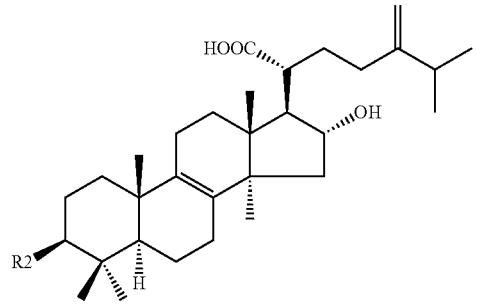

K1-1: R2 = OCOCH3 (pachymic acid)
K2-1: R2 = OH (tumulosic acid)

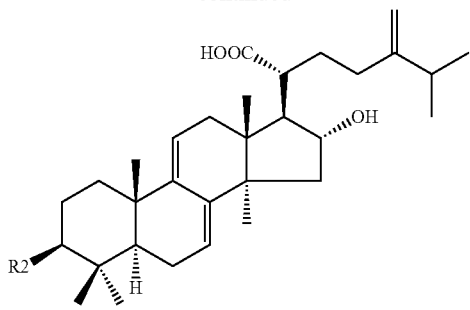

K1-2: R2 = OCOCH3 (trace quantity)
(dehydropachymic acid)
K2-2: R2 = OH (trace quantity)
(dehydrotumulosic acid)

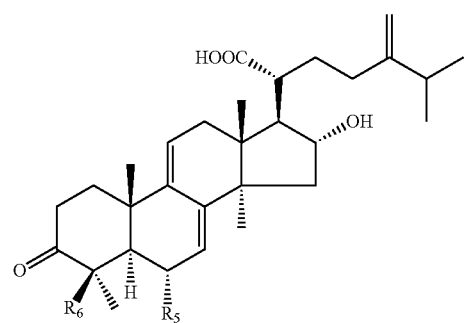

K3: R6 = CH3,
R5 = H (polyporenic acid
K4: R2 =α-OH, R5 = HC)
K4a: R6 = CH2OH, R5 = H
K6a: R6 = CH3, R5 = OH

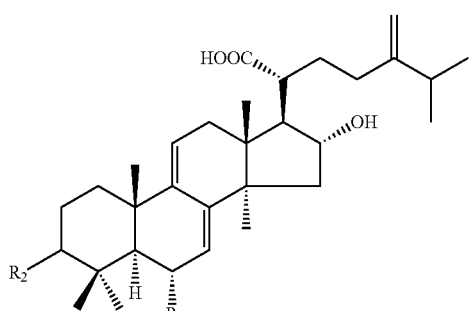

3-epidehydrotumulosic acid)
K4b: R2 = β-OCOCH3, R5 = OH

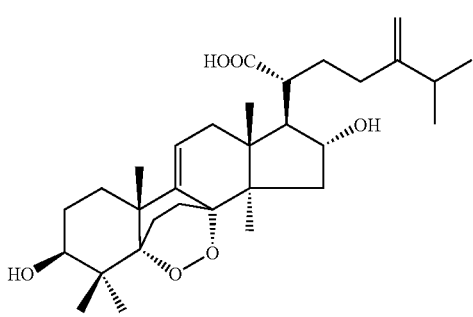

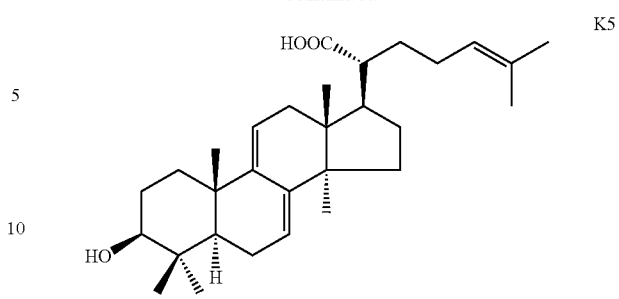

The amounts of the lanostane compounds K1 to K6b separated from the PCM portion are listed in the table below. The PCM portion contains approximately 15 wt % of the lanostane compounds K1 to K6b.

| K1 | K2 | K3 | K4 | K4a | K4b | K5 | K6a | K6b |
|---|---|---|---|---|---|---|---|---|
| 3.0 g | 6.2 g | 1.93 g | 0.55 g | 66 mg | 86.8 mg | 47.6 mg | 21.4 mg | 90.7 mg |

Example 5

Capsules having the PCM portion prepared in Example 4 were prepared basing on the following composition:

| Components | Per Capsule | Per 30,000 Capsules |
|---|---|---|
| PCM prepared in Example 4 (containing approximately 15 wt % of K1-K6 compounds) | 11.2 mg | 336.0 g |
| Sodium silicoaluminate | 5.0 mg | 150.0 g |
| Starch Potato | 378.8 mg | 11,364.0 g |
| Magnesium Sterate | 5.0 mg | 150.0 g |
| Total | 400 mg | 12,000.0 g |

The PCM portion and sodium silicoaluminate were sifted by using a #80 mesh, and the starch potato was sifted by using a #60 mesh; while magnesium sterate was sifted by using a #40 mesh. Subsequently, the aforesaid components were mixed evenly in a mixer, followed by filling the resulting mixture into No. 1 empty capsules. Each capsule contains approximately 1.68 mg (0.42 wt %) of effective components K1-K6.

Example 6

The *Poria* extracts prepared in Example 2 and 3 were formulated into an agent as shown in Table 1, as a test material to evaluate the changes of body weight, food intake and protein level in serum of animals suffering a cancer, and the overall nutritional status of patients with cachexia caused by a cancer after administration of *Poria* extract.

TABLE 1

Dose of *Poria* extract contained in the test material

| AGENT | PORIA EXTRAXCT* | ANIMAL DOSE OF LANOSTANE | CORRESPONDING HUMAN DOSE |
|---|---|---|---|
| PC-A | EXAMPLE 2 | 17.6 mg/kg | 33.6 mg/kg |
| PC-B | EXAMPLE 2 | 8.8 mg/kg | 16.8 mg/kg |
| PC-C | EXAMPLE 2 | 4.4 mg/kg | 8.4 mg/kg |
| PC-D | EXAMPLE 3 | 8.8 mg/kg | 16.8 mg/kg |

*The *Poria* extract contains 26% of lanostane compounds.

Example 7

This example is an animal test by using the agents shown in Table 1 for treating cachexia caused by a cancer. The mice having human lung cancer cell transplantation were used to clarify whether or not the *Poria* extract has a therapeutic effect on cachexia. The change of body weight, food intake and serum albumin level of mice having human lung cancer cell transplantation and normal mice were observed to evaluate the drug efficacy of treatment on cancer cachexia.

Experiment Animals

CB-17 SCID mice (6-8 weeks) were obtained from Laboratory Animal Center of the National Taiwan University (Taipei, Taiwan). Animals were kept in stainless steel cage under room temperature of 25±2° C., humidity of 40-70%, 12 hrs alternations of light and dark, without water restriction. Animals were given an adaptive phase in animal house after purchased, and animals body weight were weighed randomly. Animals with similar body weight were classified into the same group by random number, and it was confirmed that there was no significant difference of body weight between groups by statistic analysis. Cultivation of human lung cancer strain H460

H460 strain was removed from a liquid nitrogen container and thawed at 37° C. water bath. 8 mL of DMEM medium supplied with 10% FBS was taken and subjected to centrifugation at 1200 rpm for 10 mins. The supernatant was collected, to which cells were added. The cells were cultivated in a culture oven with 5% $CO_2$ at 37° C. until reaching the required cell amount.

Orthotopic Transplantation of Lung Cancer Strain H460 into Mice

Mice were deep anaesthetized by using pentobarbital, and No. 29 gauge 0.5 mL insulin needle was used to transplant 0.1 mL of H460 cell strain ($1\times10^6$/ml) into thoracic cavity of mice. Mice were housed in the original cages after cells transplantation to allow recovery.

Drug Preparation

*Poria* extract prepared in Example 2 was weighed 67.7 mg, sterilized water was added to 10 mL, and then ultrasonic treatment was performed to make the extract suspended in water, which was named PC-A agent. PC-B agent was obtained by taking 5 mL PC-A agent to adding sterilized water to 10 mL; and PC-C agent was obtained by taking 5 mL PC-B agent and adding sterilized water to 10 mL. The mice were administered according to their body weight, 0.25 cc agent/25 gm of body weigh, through tube feeding until dose shown in Table 1 was done. The test was performed twice. Mice in the Blank Group were fed with distilled water (cultivation PBS was used instead of H460 was injected into the thoracic cavity of mice). Distilled water was used to feed lung cancer mice in the Control Group. Feeding method was performed by using Injection syringe (1 cc) connected to No. 18 (5 cm length) steel tube. When tube feeding was performed, using left hand to open mice oral cavity, the tube feeding steel tube was carefully set into stomach, then an agent or distilled water was given through the tube, volume for each administration was limited to 0.3 cc.

In the first test, there were total five Groups (one Blank Group, one Control Group and three Administration Groups), 9 mice per group. Agent PC-A, PC-B and PC-C prepared by using the *Poria* extract from Example 2 were administered into the lung cancer mice of three Administration Groups, mice in each group were administered lanostane 17.6 mg, 8.8 mg and 4.4 mg per kg body weight, as shown in Table 1.

In the second test, there were total three Groups (one Blank Group, one Control Group and one Administration Group), 3 mice per group. Agent PC-D prepared by using the *Poria* extract from Example 3 was administered to the lung cancer mice of the Administration Group, wherein each mice was administered lanostane 8.8 mg per kg body weight, as shown in Table 1.

Collection of Serum Albumin Sample

Whole blood was taken from canthus at the $22^{nd}$ day, and the whole blood was kept at room temperature for one hour. After centrifugation at 3,000 rpm twice, the serum was collected and stored at −20° C. until the content analysis of serum albumin was carried out later.

Concentration Determination of Serum Albumin

Mouse albumin ELISA kit (Bethyl Laboratories Inc., Texas, US) was used to perform the analysis. Anti-mouse albumin was diluted 10× with TBS, and used to coat micro titer plate with 100 µl/well. The plate was incubated at room temperature for 1 hour, then washed with TBST three time followed by 1% BSA 200 µl/well for blocking. After incubation at room temperature for 1 hour, the plate was washed with TBST three times. Samples or standards were added, the plate was incubated at room temperature for 1 hour, followed by washing with TBST 5 times. 100 µl/well of goat anti-mouse albumin-HRP conjugate dilution (diluted 10,000× with TBS containing 1% BSA and 0.05% Tween 20) was added and incubated at room temperature for 1 hour. After washing with TBST for 5 times, 100 µl of substrate TMB (3,3',5,5'-tetramethyl benzidine) was added and reacted at dark and at room temperature for 15 minutes. 100 µl/well of 2N HCl was added to quench the reaction. The absorption at $A_{450\ nm}$ was determined.

Statistic Method

The data was represented as Mean±SD. First, one-way ANOVA was used to test the variation between the groups. If $p<0.05$, Dennett's multiple range t-test was used to test the significance of difference between the groups, wherein each group was compared to the Control Group.

Changes of Body Weight and Food Intake

The changes of food intake and body weight were observed for mice in each group in the first test and the second test.

Results

Changes of Body Weight of Mice

Figure 2:
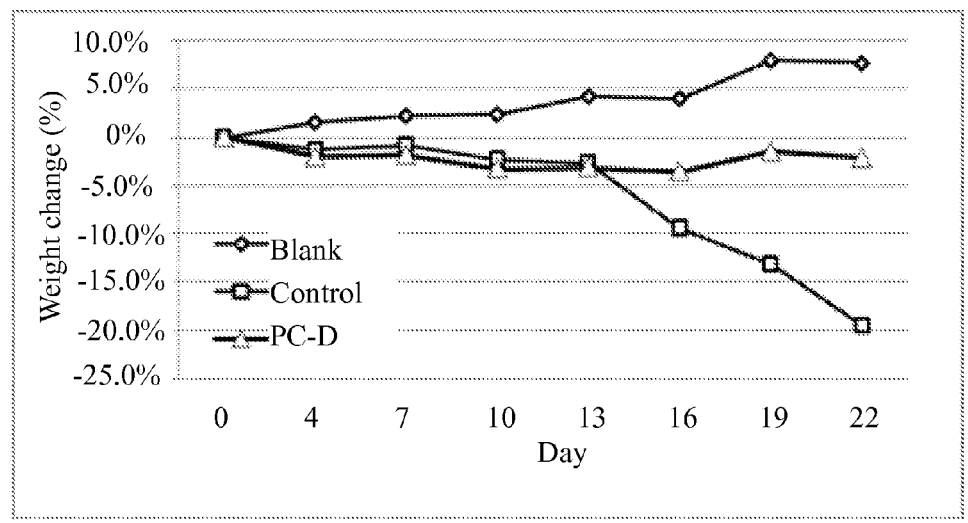
FIG. 2 shows body weight changes of mice in each group in the second test in Example 7; wherein diamond represents the blank group; square represents the control group; and triangle represents the drug administration group PC-D, wherein mice were administered lanostane in an amount of 8.8 mg per kg body weight.

In the first test, changes of body weight of lung cancer mice during tube feeding of *Poria* extract is shown as FIG. 1. Body weight of mice in the Control Group significantly decreases after the transplantation of H460 lung cancer cells. Compared to lung cancer cells transplanted mice, further administration of low dose *Poria* extract PC-C (4.4 mg/kg) and PC-B (8.8 mg/kg) do not make any difference among them. That is no improvement for cachexia syndrome. In the high dose Group (17.6 mg/kg of PC-A), it is observed that a significant slow down of body weight loss. Accordingly, the *Poria* extract improves the body weight loss caused by transplantation of H460 lung cancer. In the second test, changes of body weight of lung cancer mice using the different *Poria* extract, extract PC-D (8.8 mg/kg), is shown in FIG. 2. As shown in FIG. 1, body weight significantly decreases in the Control Group after the transplantation of H460 lung cancer cells. Only a little increase of body weight is observed in the normal mice (Blank Group without transplantation of H460 cells). It is found that mice in the Administration Group (PC-D Group) keep their body weight unchanged as at the beginning of test. Accordingly, it is proved that the *Poria* extract can be used to treat cachexia.

Changes of Food Intake of Mice with Cancer

Figure 3:
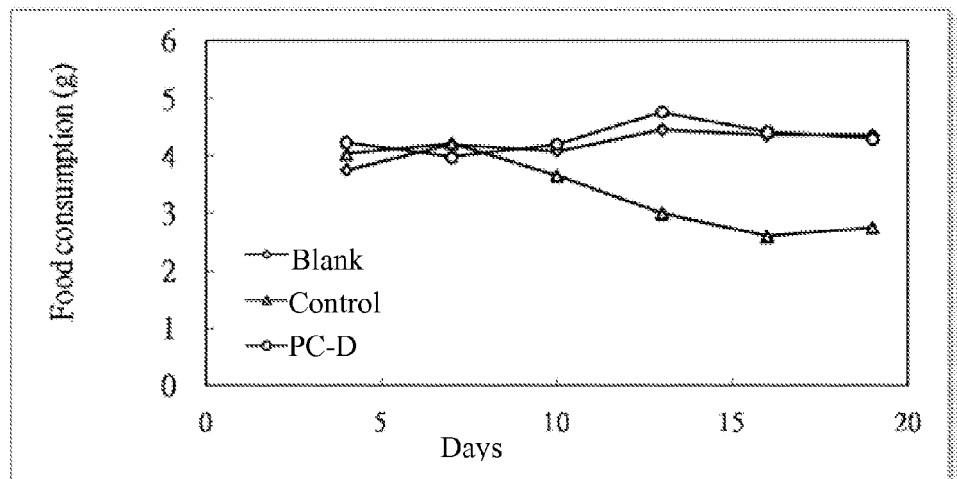
FIG. 3 shows food intake changes of mice in each group in the second test in Example 7; wherein diamond represents the blank group; triangle represents the control group; and circle represents the drug administered group PC-D, wherein mice were administered lanostane in an amount of 8.8 mg per kg body weight.

The changes of food intake of lung cancer mice after tube feeding of the *Poria* extract are shown in FIG. 3. Food intake of the mice in the Control Group gradually decreases after the transplantation of H460 lung cancer cells. Contrarily, mice in the *Poria* extract administration Group (PC-D Group) after the transplantation of lung cancer cells show no gradually decrease of food intake, similar to the normal mice in the Blank Group (without the transplantation of H460 lung cancer cells). There is no food intake difference between these two groups. Accordingly, the *Poria* extract improve or treat the impaired food intake caused by cachexia.

Changes of Serum Albumin Content of Lung Cancer Mice

Figure 4:
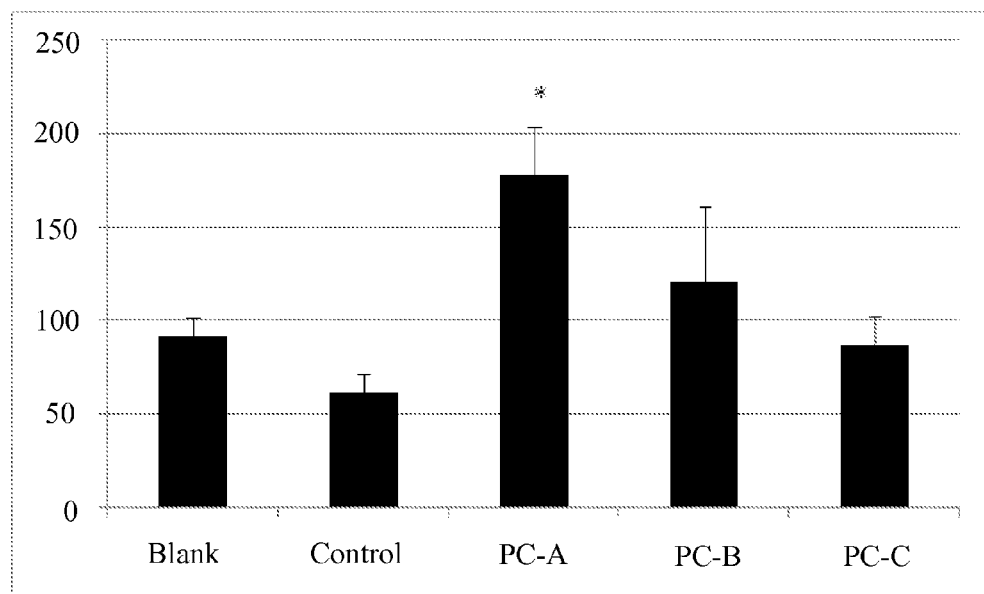
FIG. 4 shows blood albumin concentration of mice in each group in the first test in Example 7 at 22 days.
Figure 5:
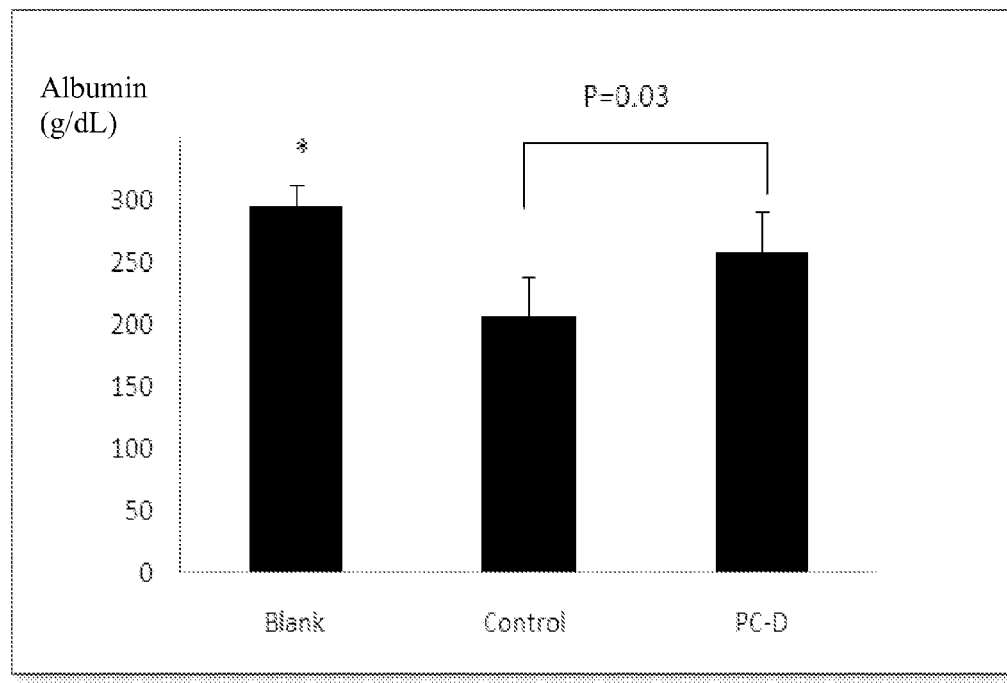
FIG. 5 shows blood albumin concentration of mice in each group in the second test in Example 7 at 22 days.

The changes of serum albumin content of mice in each group in the first test and the second test are shown in FIG. 4 and FIG. 5. Compared to the Blank Group (without H460 transplantation), mice in the Control Group with transplantation of H460 lung cancer cells have a decreasing tendency of serum albumin content. In the *Poria* extract Administration Groups (PC-A, PC-B, PC-C), the serum albumin content increases as the lanostane dose increase, and a significant increase is observed in the PC-A Group with a lanostane dose of 17.6 mg/kg. Also, a significant result is observed in the *Poria* extract Administration Group PC-D (8.8 mg/kg dose).

Animal body produces an inflammatory reaction to lung cancer cells, and this reaction changes production of hepatocyte protein, wherein some proteins decrease in production and some proteins (or induction of proteins) increase in production. Thus, one way to evaluate cachexia is to monitor serum albumin in addition to changes of body weight and food intake. The decrease of serum albumin means an influence of lung cancer cells on the albumin production in hepatocytes, and as a result the release of albumin to blood decreases. As shown in FIGS. 4 and 5, albumin content in blood decreases in mice with cachexia, but not in mice with cachexia and with the administration of the *Poria* extract. That is the *Poria* extract has a function of treating cachexia.

Example 8

Clinical study in human of *Poria* extract in treating cachexia caused by cancer:
(1) Observation of improvement of overall nutritional status in patients.
(2) Observation of improvement of body weight in patient.
  (A) Grouping of cancer patients and drug administration.

15 cancer patients with continuing body weight loss, 3 for stomach cancers, 3 for pancreas cancers, 3 for colorectal cancers, 4 for breast cancers, 1 for oral cavity cancer, and 1 for nasopharyngeal cancer, were divided in to 3 groups randomly, 5 for each group. Group I was administered with low dose *Poria* extract (Extract prepared in Example 3, 16.8 mg/capsule), one capsule per day. Group II was administered with a higher dose of *Poria* extract, two capsules per day. Group III was not administered with *Poria* extract and received chemotherapy drug as control group.

(B) Treatment Segment

Those 15 patients received chemotherapy for 6 weeks, patients in Group I and II were administered *Poria* extract for 4 weeks (for week $5^{th}$ and $6^{th}$ chemotherapy only), and the body weight and nutrition evaluation were recorded weekly.
  (C) Results (1):

An improvement of body weight was observed, a comparison of body weight was made between therapy completion (week 6 or day $42^{nd}$) and day $1^{st}$ after treatment, the results are listed as following:

| GROUP | TREATING METHOD (CHEMOTHERAPY) | BODY WEIGHT GAIN | BODY WEIGHT UN-CHANGE | BODY WEIGHT LOSS |
|---|---|---|---|---|
| GROUP I | Add 16.8 mg of *Poria* extract | 3 | 1 | 1 |
| GROUP II | Add 33.6 mg of *Poria* extract | 3 | 1 | 1 |
| GROUP III | | 1 | 0 | 4 |

From the results, it is understood that maintenance or improvement of body weight in the chemotherapy/*Poria* extract Groups were superior than in Group III (only chemotherapy without *Poria* extract). A body weight loss was observed in Group III, i.e. the boy weight lower than the $1^{st}$ day after treatment.

(D) Results (2): Improvement of Overall Nutritional Status in Patients

Figure 6:
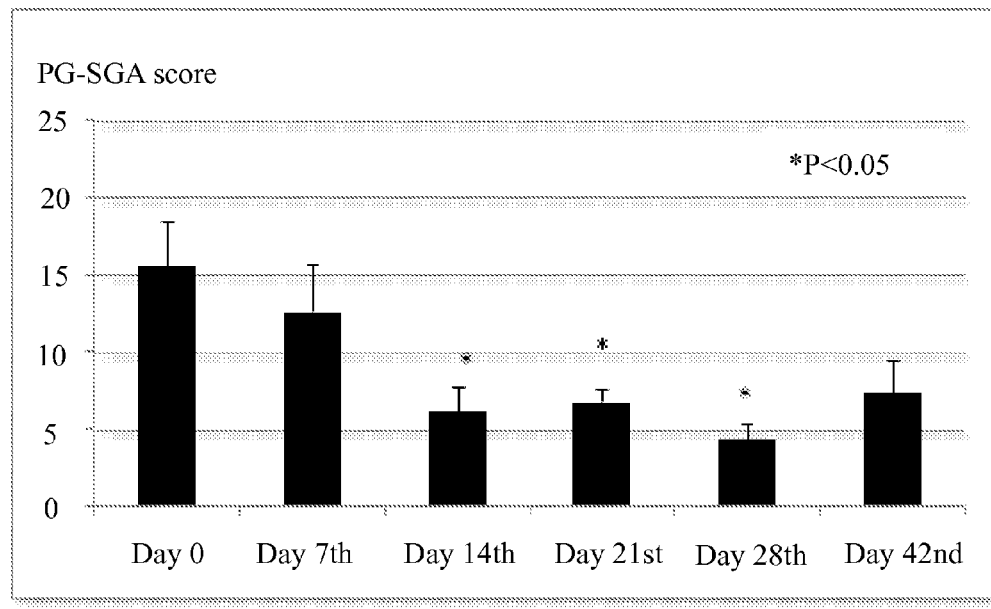
FIG. 6 shows evaluation of overall nutritional status of Group I cancer patients (chemotherapy+one *Poria* extract capsule) in Example 8, who were evaluated by according to PG-SGA assessment (Patient-Generated Subjective Global Assessment) used by clinician.
Figure 7:
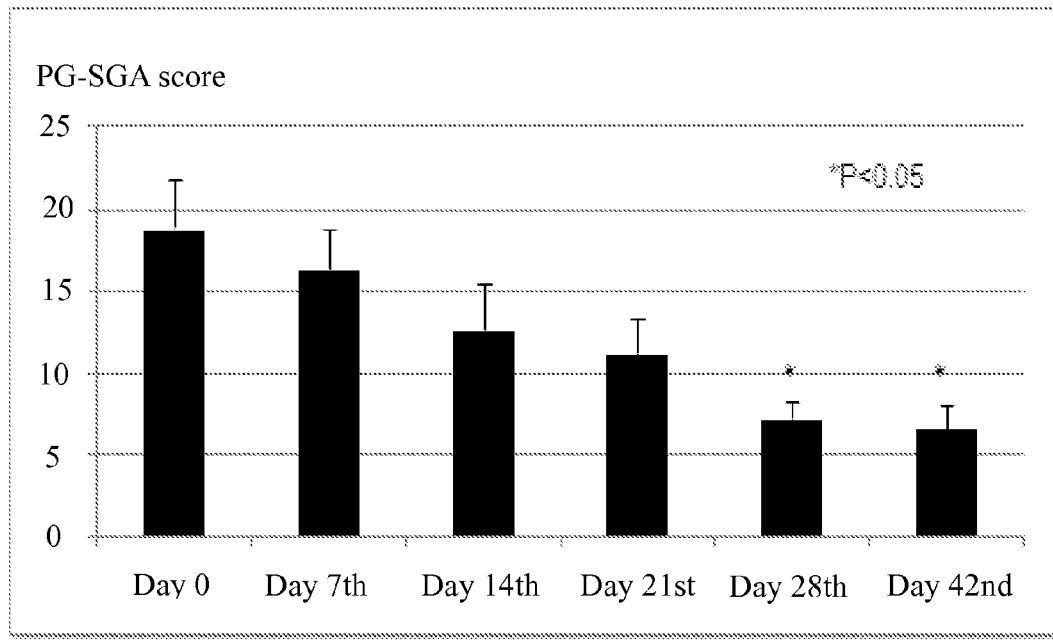
FIG. 7 shows evaluation of overall nutritional status of Group II cancer patients (chemotherapy+two *Poria* extract capsules) in Example 8, who were evaluated according to PG-SGA assessment used by clinician.
Figure 8:
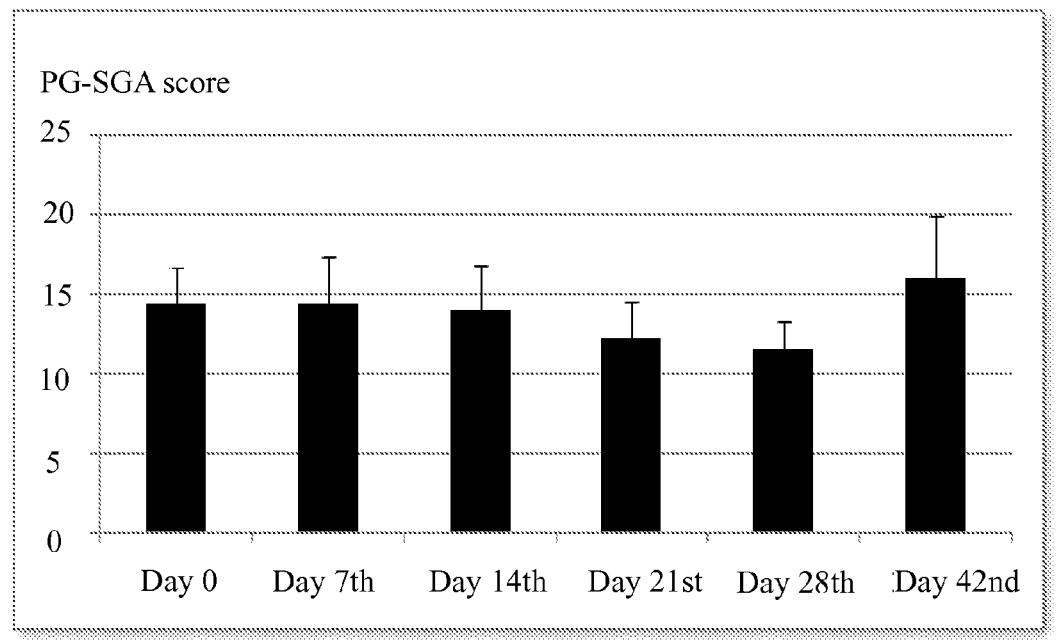
FIG. 8 shows evaluation of overall nutritional status of control group cancer patients (chemotherapy) in Example 8, who were evaluated according to PG-SGA assessment used by clinician.

The evaluation of overall nutritional status of patients was made according to PG-SGA (Patient-Generated Subjective Global Assessment) used by the clinician. Patients of Groups I to III were evaluated by gaining the total scores of (1) body weight improvement, (2) food intake improvement, (3) syndrome alleviation and (4) physical activity improvement, as shown in FIGS. 6, 7, and 8. FIG. 6 is the results observed in Group I (chemotherapy+one capsule of *Poria* extract), FIG. 7 is the results observed in Group II (chemotherapy+two capsules of *Poria* extract), and FIG. 8 are results observed in Group III (control group, chemotherapy). The lower score of PG-SGA, the more improvement in patients, overall tendency directs forward to healthy.

From these treating results, the improvement for cachexia patients in health/living quality observed in the groups administered with *Poria* extract combined with chemotherapeutic drug is significantly better that observed in the chemotherapy Group, and there is a significant meaning in statistic analysis.

According to the results of this Example, it is found that a combination of *Poria* extract and chemotherapy drug can inhibit body weight loss of cancer patients, while the improvement in the overall nutritional status of the patients is significantly superior to the patients only receive chemotherapy.

The present invention has been described with preferred examples thereof and it is understood that many changes and modifications to the described examples can be carried out without departing from the scope and the spirit of the invention that is intended to be limited only by the appended claims.

What is claimed is:

1. A method for prophylaxis or treatment of a wasting disease, comprising administering to a mammal in need thereof an effective amount of a lanostane compound of formula (I):

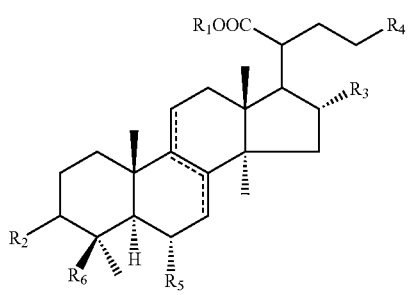

(I)

wherein $R_1$ is —H or —$CH_3$; $R_2$ is —$OCOCH_3$, =O, or —OH; $R_3$ is —H or —OH; $R_4$ is —C(=$CH_2$)—C($CH_3$)$_2$$R_a$, or —CH=C($CH_3$)$R_b$, in which $R_a$ is —H or —OH, and $R_b$ is —$CH_3$ or —$CH_2OH$; $R_5$ is —H or —OH; and $R_6$ is —$CH_3$ or —$CH_2OH$, or a pharmaceutically acceptable salt thereof.

2. The method of claim 1, wherein the lanostane compound of formula (I) is:

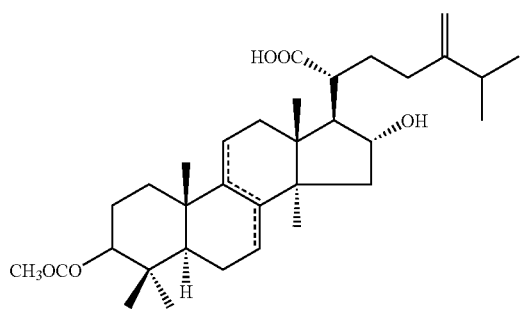

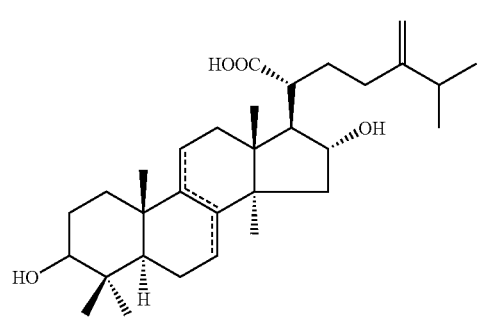

or

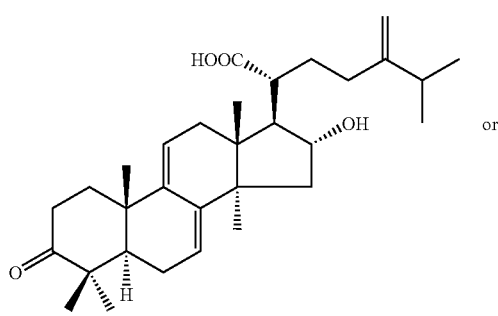

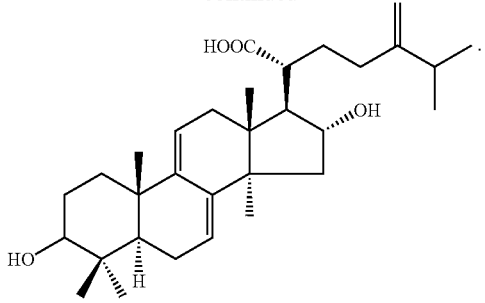

3. The method of claim 1, wherein the lanostane compound of formula (I) or a pharmaceutically acceptable salt thereof is administered to the mammal as a *Poria* extract comprising 1-60% of the lanostane compound of formula (I), based on the weight of the *Poria* extract.

4. The method of claim 1, wherein the lanostane compound of formula (I) or a pharmaceutically acceptable salt thereof is administered to the mammal as an isolated compound together with a pharmaceutical acceptable carrier or diluent.

5. The method of claim 1, wherein the lanostane compound of formula (I) is administered orally.

6. The method of claim 1, wherein the wasting disease is cachexia.

7. The method of claim 1, wherein the mammal is a human.

8. The method of claim 3, wherein said *Poria* extract is substantially free of secolanostane.

9. The method of claim 8, wherein said *Poria* extract comprises, based on the weight of the *Poria* extract, 5-35% of the lanostane compound of formula (I).

10. The method of claim 8, wherein the lanostane compound of formula (I) has the following chemical formula:

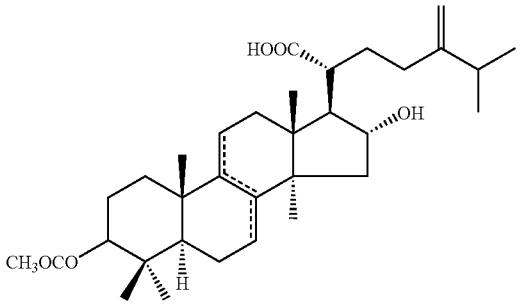

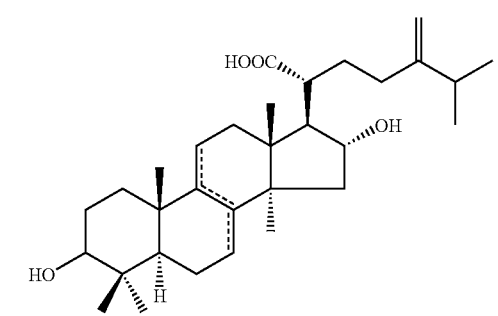

-continued

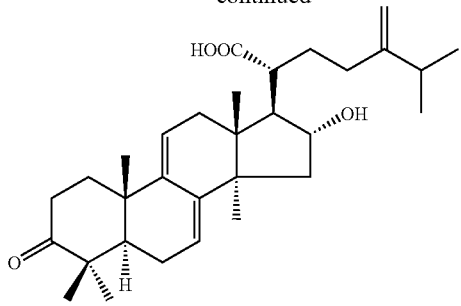

or

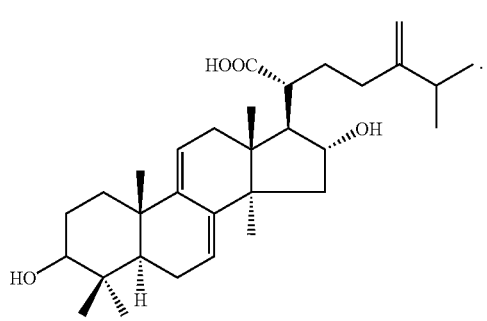

11. The method of claim 6, wherein the cachexia is cancer cachexia.

12. The method of claim 11, wherein said cancer is lung cancer, stomach cancer, pancreas cancer, colorectal cancer, breast cancer, oral cavity cancer, or nasopharyngeal cancer.

13. The method of claim 1, wherein the wasting disease is caused by cancer, anorexia, aging, body injury, or body burn.

14. The method of claim 1, wherein the lanostane compound of formula (I) or a pharmaceutically acceptable salt thereof is administered to a human being in an amount of not less than 8.4 mg/day.

15. The method of claim 1, wherein the wasting disease is caused by AIDS, aging, rheumatoid arthritis, pulmonary tuberculosis, fibrocyst, or crohn's disease.

16. The method of claim 1 further comprising administering a nutritional supplement, wherein the lanostane compound of formula (I) improves uptake of the nutritional supplement.

17. The method of claim 16, wherein the nutrient supplement is an amino acid, glucose, a vitamin, or a combination thereof.

18. The method of claim 16, wherein the wasting disease is caused by AIDS, aging, rheumatoid arthritis, pulmonary tuberculosis, fibrocyst, or crohn's disease.

19. The method of claim 16, wherein the lanostane compound of formula (I) is:

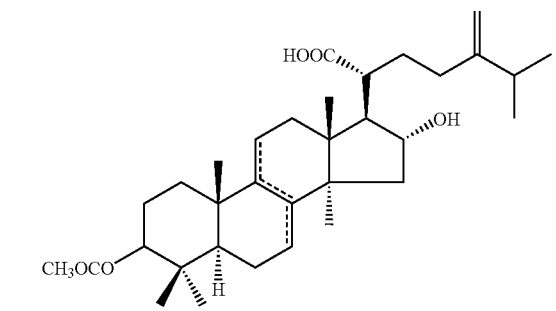

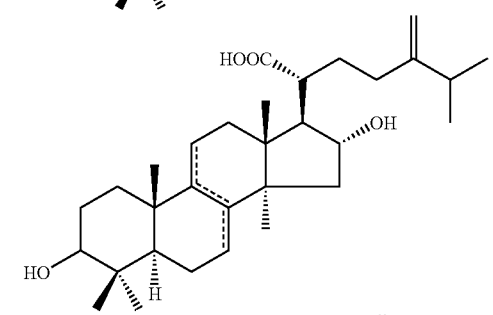

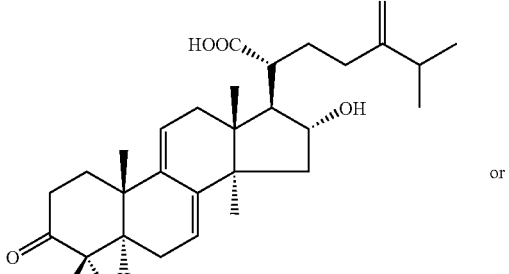

or

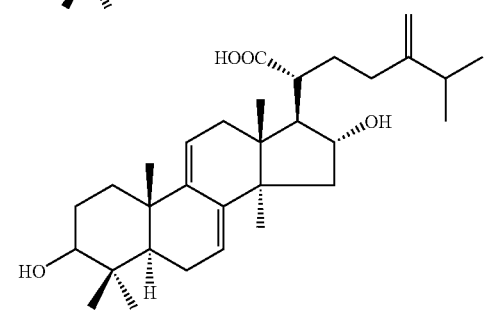

20. The method of claim 12, wherein the cancer is stomach cancer, pancreas cancer, colorectal cancer, breast cancer, oral cavity cancer, or nasopharyngeal cancer.

* * * * *